United States Patent [19]

Shimada et al.

[11] Patent Number: 4,845,215

[45] Date of Patent: Jul. 4, 1989

[54] PURINE DERIVATIVE

[75] Inventors: Nobuyoshi Shimada, Tokyo; Takayuki Tomizawa, Machida; Shigeru Hasegawa, Yono; Kaoru Matsuo, Kashiwa; Akio Fujii, Kamakura; Hiroo Hoshino, Maebashi, all of Japan

[73] Assignee: Nippon Kayaku Kabushiki Kaisha, Tokyo, Japan

[21] Appl. No.: 54,192

[22] Filed: May 26, 1987

[51] Int. Cl.$^4$ .................. C07D 473/32; A61K 31/52
[52] U.S. Cl. ................................................. 544/265
[58] Field of Search ............... 544/267, 276, 265, 277; 514/262

[56] References Cited

U.S. PATENT DOCUMENTS

| | | | |
|---|---|---|---|
| 3,180,859 | 4/1965 | Hoeksema et al. | 544/265 |
| 4,452,788 | 6/1984 | Bristol et al. | 514/263 |
| 4,742,064 | 5/1988 | Vince | 514/298 |

FOREIGN PATENT DOCUMENTS 0182315  5/1986  European Pat. Off. .

OTHER PUBLICATIONS

Shimada, et al., "Oxetanocin, A Novel Nucleoside From Bacteria", The Journal of Antibiotics, vol. 39, No. 11, pp. 1623–1625, Nov. 1986.

*Primary Examiner*—Nicholas S. Rizzo
*Attorney, Agent, or Firm*—Henry C. Nields

[57] ABSTRACT

The present invention relates to a novel compound having hypoxanthine base represented by the following formula:

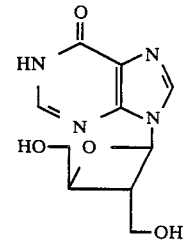

as well as to use of said compound and process for producing said compound.

The novel compound of the present invention has an immunosuppressive and antiviral actions and is expected to be useful as a medical drug.

1 Claim, 1 Drawing Sheet

PURINE DERIVATIVE

BACKGROUND OF THE INVENTION

1. Field of the Invention

The present invention relates to a novel compound having hypoxanthine base, its use and a process for producing it.

2. Description of the Prior Art

The deamination by adenosine deaminase is known, with regard to adenosine and 2′-deoxyadenosine which are purine nucleosides, as well as to Cordyceptin and Formycin which are purine nucleoside antibiotics [Journal of Antibiotics, Vol. 18, Ser. A, Page 191 (1965)].

In the field of viral infectious diseases, novel substances are always waited for because of the infinite variety in the character of such diseases. Particularly, antiviral agents having a growth-inhibitory effect on AIDS virus [internationally, it is proposed to call this virus "Human Immunodeficiency Virus (HIV)"] and B type viral hepatitis are desired.

Further, with the increases in transplantation of internal organs and autoimmune diseases, development of novel immunosuppressants are desired.

SUMMARY OF THE INVENTION

After many studies, the present inventors discovered that a novel compound having hypoxanthine base represented by the following formula (1):

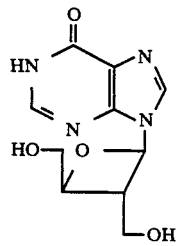

has an antiviral action and an immunosuppressive action. Based on this finding, the present invention was accomplished.

BRIEF DESCRIPTION OF THE DRAWING

The accompanying drawing is a ¹H-nuclear magnetic resonance spectral chart of the compound of the present invention, i.e. 9-[(2′R,3′R,4′S)-3′,4′-bis-(hydroxymethyl)-2′-oxetanyl]-hypoxanthine, measured in deutero dimethyl sulfoxide by using tetramethylsilane as the internal standard substance.

DETAILED DESCRIPTION OF THE INVENTION

Figure 1:
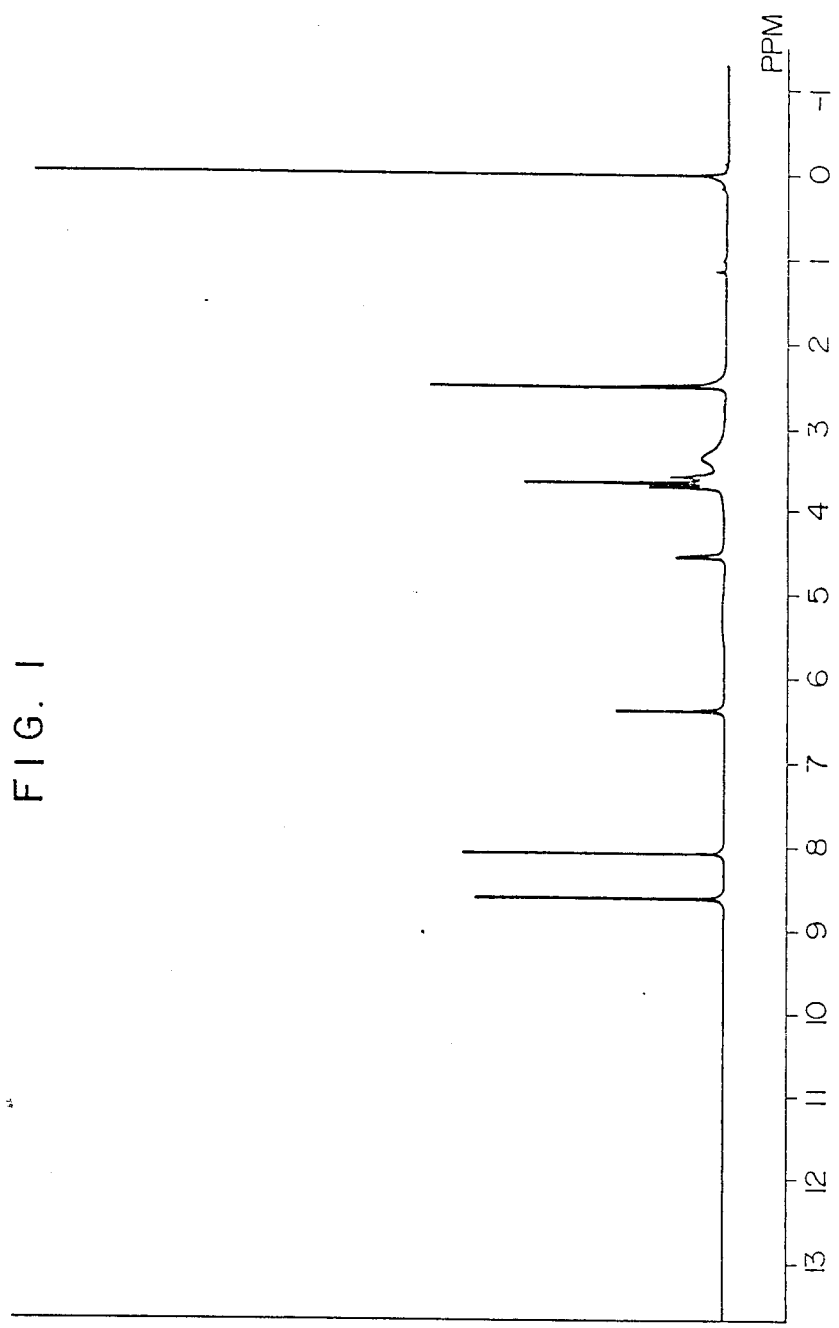

The compound of the present invention can be produced in the following manner. Thus, adenosine deamine or a substance having the same ability as that of adenosine deamines which has been collected from cultured product of microorganism, its treated product or animal tissue is made to act upon a compound having adenine base represented by the following formula (2):

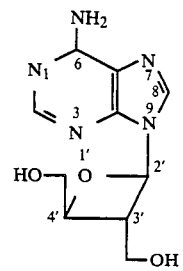

whereby a novel compound having hypoxanthine base represented by the following formula (1) can be obtained:

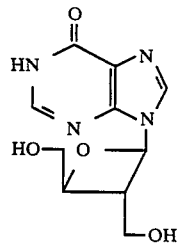

This reaction is carried out in a buffer having a pH value of about 5 to about 9 (preferably about 6 to about 8 and usually at about 7) at a temperature of 0° C. to 90° C. and preferably 5° C. to 70° C.

The adenosine deaminase used in the present invention may be a commercial product. As concrete example of the commercial product, EC3, 5, 4, 4 manufactured by Sigma Co. can be referred to. Apart from it, a substance collected from animal tissue, a cultured product of microorganism, the adenosine deaminase collected from these materials and the like, having a similar ability, are also usable for this purpose regardless of their origin. As for the enzyme, it is not always necessary to use a purified enzyme. When an enzyme originated from microorganism is to be used, a cultured product of microorganism (cell) obtained by culturing a microorganism having an ability to produce adenosine deaminase in a nutrient medium can also be used as it is. Apart from it, crude enzymes prepared from acetone-dried cell of microorganism, mashed product of microorganism cell and ultrasonic wave-treated product of microorganism cell, as well as surfactant-treated, toluene-treated and lysozyme-treated products of microorganism cell, are similarly usable. Microorganism cell fixed on a synthetic polymer is also usable. Concretely saying, the following microorganisms can be used.

*Alkaligenes bookeri* IFO 12948
*Escherichia coli* NIHJ
*Escherichia coli* 120551
*Escherichia coli* 120595
*Escherichia coli* 120628
*Citrobacter freundii* GN 346
*Proteus morganii* IFO 3168
*Elytrosporanim brasiliense* IFO 1259
*Norcardia asteroides* IFO 3423
*Streptomyces alboniger* IFO 12738
*Streptomyces californicus* IFO 12750
*Streptomyces chrestomyceticus* IFO 13444
*Streptomyces subsp lasaliensis* ATCC 31180
*Streptomyces tubercidicus* IFO 13090
*Streptomyces verticillus* ATCC 31307

*Aspergillus niger* IFO 4066
*Fusarium roseum* IFO 7189
*Penicillium chrysogenum* JBI-FI
*Penicillium chrysogenum* 51-20T In producing the compound of formula (1) in the present invention the compound of formula (2) and adenosine deaminase are reacted in a phosphate buffer having a concentration of about ½ M to about 1/30 M (preferably about 1/10 M) (pH about 5 to about 9, preferably about 7.0) at a temperature of about 5° to 70° C. (preferably about 20° to 30° C., usually 25° C.), for a period of 10 minutes to 50 hours (preferably 30 minutes to 10 hours, usually several hours). By this reaction, the intended compound of formula (1) is formed in the reaction mixture. When a cultured microorganism is used, the microorganism shown in Table 1 is cultured in a nutrient medium for 24 hours, after which the cultured product may be used directly. Preferably, however, the cultured alive cells are collected by centrifugation and suspended into M/20 phosphate buffer (pH 7.0), and the resulting suspension is mixed with the compound of formula (2) (oxetanocin) and reacted at a temperature of 20° to 70° C. for at most 20 hours, whereby the intended compound of formula (1) is formed in the reaction mixture. The product can be taken out of the reaction mixture according to the usual method. That is, it can be collected by a method which comprises removing inactive substances by centrifugation or the like and then isolating the intended product by utilizing solubility difference into water or organic solvent or by an absorption-desorption method using active charcoal, adsorption resin or ion exchange resin, or by appropriate combination of these methods.

For example, the compound of formula (2) is reacted with the above-mentioned enzyme or the washed cell shown in Table 1, and then inactive substance or the useless microorganism cell is removed by centrifugation. The supernatant is passed through a column of porous resin to have the product adsorbed on the resin. After washing the column with water, the product is eluted with hydrated methanol and the eluate is concentrated and evaporated to dryness. Thus, the compound of formula (1) is obtained in the form of a colorless powder. If desired, Sephadex resins are also usable.

The compound of formula (2) used in the present invention as starting material is a known compound by the Journal of Antibiotics Vol. 39, No. 11, pp 1623–1625 and pp 1626–1629, Nov. 1986, and this compound can be obtained by culturing NK 84-0218 strain belonging to Genus Bacillus (FERM BP-919) in a nutrient medium and isolating the formed and accumulated compound of formula (2) in the usual way. The compound of formula (2) thus obtained is 9-[(2'R,3'R,4'S)-3',4'-bis(hydroxymethyl)-2'-oxetanyl]-adenine (oxetanocin).

Salts of the compounds of formula (1) can be obtained by dissolving it into an aqueous solution of strong acid such as hydrochloric acid, sulfuric acid and the like (pH about 2) by, for example, heating, etc. and cooling or adding a soluble solvent with water to precipitate the resulting salt therefrom.

The compound of formula (1) obtained herein, i.e. 9-[(2'R,'R,4'S)-3',4'-bis(hydroxymethyl)-2'-oxetanyl]-hypoxanthine, has the following physico-chemical properties:

(1) Appearance
Colorless and powdery
(2) Elementary analysis (%) ($C_{10}H_{12}O_4N_4$)

|  | C | H | O | N |
|---|---|---|---|---|
| Calculated | 47.62 | 4.80 | 25.37 | 22.21 |
| Found | 47.41 | 4.96 | 25.58 | 22.05 |

(3) Molecular formula (molecular weight)
$C_{10}H_{12}O_4N_4$ (252.24)
(4) Melting point
203°–205° C.
(5) Specific optical rotation
$[\alpha]_D^{20} = -8.8°$ (C=0.455, $H_2O$)
(6) Ultraviolet absorption spectrum Ultraviolet absorptions and molar absorptivities in water, 0.1 N hydrochloric acid and 0.1 N sodium hydroxide solution are as follows:

| | |
|---|---|
| $\lambda_{max}^{H_2O}$ (log ε) = 248.5 | nm (4.10) |
| $\lambda_{max}^{0.1N\ Hcl}$ (log ε) = 249 | nm (4.08) |
| $\lambda_{max}^{0.1N\ NaOH}$ (log ε) = 253 | nm (4.12) |

(7) Infrared absorption spectrum
The absorption maxima (wave number $cm^{-1}$) in the infrared absorption spectrum measured in potassium bromide tablet are as follows:

| | | | | | |
|---|---|---|---|---|---|
| 3400 | 3120 | 2870 | | | |
| 1695 | 1590 | 1552 | 1515 | 1492(sh) | 1465(sh) |
| 1450 | 1420 | 1376 | 1340 | 1320(sh) | 1250(sh) |
| 1220 | 1150 | 1120(sh) | 1100 | 1050(sh) | 1012 |
| 970 | 900 | 845 | 788 | 720(sh) | 685 |

(8) Solubilities into solvents
It is soluble in water, methanol and dimethyl sulfoxide and insoluble or only slightly soluble in propanol, acetone, ethyl acetate, ether and benzene.
(9) Color reactions
It is positive in Rydon-Smith reaction and 10% sulfuric acid reaction, while it is negative in ninhydrin reaction.
(10) Rf value in thin layer chromatography
If silica gel thin layer (Kiesel gel 60 F254, 0.25 mm, Merck) is used and development is carried out with n-butanol : acetic acid : water (4 : 1 : 2) or n-butanol : 28% aqueous ammonia : water (10 : 0.5 : 1), Rf=0.43 or 0.10, respectively.
(11) $^1H$-Nuclear magnetic resonance spectrum
FIG. 1 illustrates the $^1H$-nuclear magnetic resonance spectrum measured in deutero dimethyl sulfoxide by using tetramethylsilane as an internal standard substance.
(12) $^{13}C$-Nuclear magnetic resonance spectrum
Chemical shiftes (δvalues) in the $^{13}C$-nuclear magnetic resonance spectrum measured in heavy water by using dioxane (δ67.4) as internal standard substance are as follows:
159.7, 149.2, 147.3, 141.3, 124.5, 82.8, 80.4, 63.3, 59.8, 45.5

As mentioned later, the compound of the present invention represented by formula (1) is expectedly useful as a medical drug having immunosuppressive action and antiviral activity for animal including human. When it is used as a medical drug, the method for preparing its composition and the method of its administration to the animal may be hitherto known methods.

That is, as the method of administration, injection, oral administration, intrarectal administration and the like can be adopted. As the form of composition, injection, powder, granule, tablet, suppository and the like can be adopted.

In preparing the composition, various adjuvants usable in medical drugs, such as vehicle and other assistants (e.g. stabilizer, antiseptic, soothing agent, emulsifier and the like) are used depending on what is desired, unless they exercise adverse influence upon the compound of formula (1).

In preparing the composition, the content of compound (1) can be varied in a wide range, depending on the form of composition, etc. Generally saying, the composition contains the compound of formula (1) in an amount of 0.01 to 100% by weight (preferably 0.1 to 70% by weight), and the residual part of the composition consists of vehicle and other adjuvants conventionally used in medical drugs.

Although the dose of the compound of formula (1) varies depending on symptoms, it is about 0.01 to 800 mg per day per one person in the case of adult. When continual administration is necessary, the dose is preferably lessened.

In preparing the composition, the compound of formula (1) is usually used in the form of medically acceptable salt, such as hydrochloride and sulfate.

Physiological activity (1) Next, the antiviral activity of the compound represented by formula (1) will be mentioned.

(a) Its antiviral activity was measured by observing CPE (cytopathic effect) of Herpes Simplex virus type-II on the Vevo cell originated from the kidney of *Cercopithecus aetiops*.

| TCID$_{50}$ Concentration (mcg/well) | 87.5 mcg/well Inhibition rate (%) |
| --- | --- |
| 125 | 75 |
| 62.5 | 33 |
| 31.3 | 8 |

(b) Anti-"Human Immunodeficiency Virus (HIV)" activity.

About 100,000 cells/ml of MT-4 cell was introduced into a tray having 24 holes. Further, 100 microliters of a solution containing a predetermined quantity of the compound of the present invention was added, and then it was cultured in a 5% (v/v) carbon dioxide gas incubator at 37° C. for 5 hours. Subsequently, $10^3$ to $10^4$ infection units of HIV was added and cultured for 4 days. Then, a part of the culture fluid was applied to a slide glass and immobilized with acetone, and development of virus antigen was examined by the fluorescent antibody technique.

A serum of an AIDS patient was used as the primary antibody of the fluorescent antibody technique, and FITC-labelled anti-human IgG was used as its secondary antibody.

Cytopathic effect of the compound of the invention on MT-4 cell was examined microscopically without adding virus.

| Activity of the compound of the invention on HIV | | |
| --- | --- | --- |
| Concentration (μg/ml) | Cytopathic effect | Development of virus antigen (%) |
| 100 | — | 2 |
| 10 | — | 10 |
| 1 | — | 40 |

Note:
The compound of the present invention was used in the form of a solution in DMSO. In DMSO itself only, development of virus antigen was 80 to 90%.

As is apparent from the above-mentioned results, the compound of the present invention has a marked growth-inhibitory action of HIV and its cytopathic effect is small.

(2) Next, the immunosuppressive action of the compound of the present invention represented by formula (1) will be mentioned.

Inhibition of Blastogenesis Reaction of T Lymphocyte by Con A.

Spleen cell of BALB/C mouse was dividingly poured into a microplate so that the number of cells came to $2 \times 10^5/0.2$ ml/well. To each of all the wells other than control group was added the compound of the present invention having varied concentration. Further, 5 micrograms/liter of Con A was added to all the wells. Then, the cell suspensions were cultured at 37° C. for 72 hours in 5% carbon dioxide gas incubator. The blastogenesis reaction of lymphocyte was examined by adding 1μCi/well of $^3$H-thymidine 6 hours before the completion of the culture and measuring its take-up into cultured cells by means of liquid scintillation counter. If the take-up count at the time when only Con A was added was expressed by Adpm and the take-up count at the time when Con A and drug were added was expressed by Bdpm, (1 - Bdpm/Adpm)×100 could be regarded as the inhibitory rate of each drug on blastogenesis. IC$_{50}$ (mcg/ml) was measured, and it was found that IC$_{50}$ of the compound of the present invention was 14.5 mcg/ml.

Since the compound of the present invention has an immunosuppressive action, an immunosuppressant containing the compound of the present invention as its active ingredient is considered quite useful for controlling the rejection probably caused by abnormally exasperated immune in the transplantation of organs or transplantation of the skin, for treating various autoimmunization diseases of which main cause is considered auto-immunization, such as multiple sclerosis, hemolytic anemia, I-type diabetes, myasthenia gravis, Hashimoto thyreoiditis, Paget syndrome and rheumatism, and for treating the allergic diseases.

(3) The acute toxicity (LD$_{50}$) of the compound of formula (1) on mouse was 200 mg/kg (iv) or above which is weaker than the toxicities of various known nucleic acid type antibiotics.

EFFECT OF THE INVENTION

It is apparent from the above-mentioned results that the compound of the present invention represented by formula (1) has an antiviral activity. Further, since it is different in chemical structure from the hitherto known nucleic acid type antibiotics, it is expectedly useful as a novel antiviral agent having a novel action mechanism for use in the treatment of various viral diseases such as herpes, AIDS, B type hepatitis and the like. Further, since it has an immunosuppressive activity, it is expectedly usable as an immunosuppressant.

Next, examples of the present invention will be mentioned. The examples herein presented are nothing other than merely illustrative examples and they are by no means limitative, so that their many modifications are possible.

EXAMPLE 1

Into 39 ml of M/10 phosphate buffer was dissolved 78 mg of the compound of formula (2). Then, 25 microliters (9.9 units) of adenosine deaminase (EC3, 5, 4, 4; manufactured by Sigma Co.) was added thereto and reacted at 25° C. for 5 hours with stirring, after which the reaction mixture was heated at 100° C. for 5 minutes to stop the reaction. Then, the reaction mixture was passed through a column packed with 50 ml of MCI Gel®CHP-20P to have the product adsorbed on the column. After washing the column with water, the product was eluted with 150 ml of methanol containing 20% of water, concentrated and evaporated to dryness to obtain 69 mg (yield 88.1%) of a colorless and powdery compound of formula (1).

EXAMPLE 2

One hundred mililiters of a medium containing 0.3% of meat extract, 1.0% of peptone and 0.7% of sodium chloride (pH=7.0) was dividingly poured into 500 ml Erlenmeyer flasks and sterilized in an autoclave at 120° C. for 20 minutes. The content of each flask was inoculated with one platinum quantity of Escherichia coli NIHJ and subjected to an aerobic shaking culture at 37° C. for 18 hours. Then, 1,000 ml of the culture fluid was centrifuged at 10,000 r.p.m. for 10 minutes to collect the alive bacterial cell. It was washed with three 1,000 ml portions of M/20 phosphate buffer (pH 7.0) and then suspended into 100 ml of the same buffer as above. Fifty milligrams of the compound of formula (2) was added to the suspension and reacted at 37° C. for 18 hours with shaking, after which the reaction mixture was heated at 100° C. for 5 minutes to stop the reaction. After removing the bacterial cell by centrifugation under the same conditions as above, the supernatant was passed through a column packed with 50 ml of MCI Gel®CHP-20P to have the product adsorbed on the column. After washing the column with water, the product was eluted with 150 ml of methanol containing 20% of water, concentrated and evaporated to dryness. Thus, 43.0 mg (yield 86.0%) of a colorless and powdery compound of formula (1) was obtained.

EXAMPLE 3

The same treatment as in Example 2 was carried out by the use of microorganism. Conversion (%) of the compound of formula (2) to the compound of formula (1) in the reaction mixture was as shown in the following table.

| Kind of microorganism | Reaction temperature 37° C. | 60° C. |
|---|---|---|
| Alkaligenes bookeri IFO 12948 | 54.0 | 0 |
| Escherichia coli NIHJ | 99.6 | 97.7 |
| Escherichia coli 120551 | 100 | 100 |

-continued

| Kind of microorganism | Reaction temperature 37° C. | 60° C. |
|---|---|---|
| Escherichia coli 120595 | 100 | 100 |
| Escherichia coli 120628 | 89.2 | 0 |
| Citrobacter freundii GN 346 | 98.6 | 100 |
| Proteus morganii IFO 3168 | 100 | 95.9 |
| Elytrosporanim brasiliense IFO 1259 | 40.4 | 31.9 |
| Nocardia asteroides IFO 3423 | 24.0 | 27.1 |
| Streptomyces alboniger IFO 12738 | 0 | 21.5 |
| Streptomyces californicus IFO 12750 | 0 | 43.0 |
| Streptomyces chrestomyceticus IFO 13444 | 0 | 22.3 |
| Streptomyces subsp lasaliensis ATCC 31180 | 0 | 43.8 |
| Streptomyces tubercidicus IFO 13090 | 66.7 | 30.3 |
| Streptomyces verticillus ATCC 31307 | 67.6 | 49.4 |
| Aspergillus niger IFO 4066 | 48.0 | 0 |
| Fusarium roseum IFO 7189 | 74.7 | 0 |
| Penicillium chrysogenum JBI-FI | 11.6 | 0 |
| Penicillium chrysogenum 51-20T | 89.8 | 0 |

Next, examples of the composition of the present invention will be mentioned below.

Composition Example 1: Injection

Purified water was added to 30 parts by weight of hydrochloride of the compound of formula (1) and the total volume was adjusted to 2,000 parts. After complete dissolution, the resulting solution was sterilized by filtering it through Millipore filter of GS type. Two grams of the filtrate was taken into a 10 ml vial and freeze-dried. Thus, a freeze-dried injection containing 30 mg of Compound (1) per one vial was obtained.

Preparation Example 2: Granule

A mixture consisting of 50 parts by weight of Compound (1), 600 parts of lactose, 330 parts of crystalline cellulose and 20 parts of hydroxypropyl cellulose was thoroughly homogenized, pressed by means of roll type press (Roller Compacter®), crushed, and sieved. The fraction between 16 meshes and 60 meshes was taken and used as granule.

Preparation Example 3: Tablet

A mixture consisting of 30 parts by weight of Compound (1), 120 parts of crystalline lactose, 147 parts of crystalline cellulose and 3 parts of magnesium stearate was formed into tablet by means of V-type blender. Thus, a tablet containing 300 mg of Compound (1) was obtained.

What is claimed is:

1. A compound having hypoxanthine base represented by the following formula:

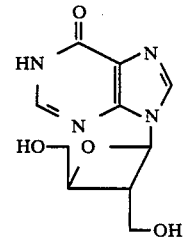

* * * * *